United States Patent [19]

Witzel et al.

[11] Patent Number: 5,344,983
[45] Date of Patent: Sep. 6, 1994

[54] SELECTIVE PREPARATION OF LINEAR PENTANE-1,5-DIAMINES IN INCREASED YIELDS

[75] Inventors: Tom Witzel; Eberhard Fuchs, both of Ludwigshafen; Franz Merger, Frankenthal; Claus-Ulrich Priester, Ludwigshafen, all of Fed. Rep. of Germany

[73] Assignee: BASF Aktiengesellschaft, Ludwigshafen, Fed. Rep. of Germany

[21] Appl. No.: 936,084

[22] Filed: Aug. 26, 1992

[30] Foreign Application Priority Data

Sep. 4, 1991 [DE] Fed. Rep. of Germany ....... 4129350

[51] Int. Cl.$^5$ ............................................. C07C 209/00
[52] U.S. Cl. .................................... 564/396; 564/398; 564/446; 564/471; 564/448; 546/184; 546/244; 528/87
[58] Field of Search ......................... 528/87, 396, 398; 564/446, 448, 471; 546/184, 244

[56] References Cited

U.S. PATENT DOCUMENTS

| | | | |
|---|---|---|---|
| 3,728,353 | 4/1973 | Groen et al. | 546/184 |
| 4,098,846 | 7/1978 | Olander | 528/212 |
| 4,100,111 | 7/1978 | Peter et al. | |
| 4,386,208 | 5/1983 | Rebafka et al. | 546/184 |
| 4,429,157 | 1/1984 | Disteldorf et al. | 564/446 |

FOREIGN PATENT DOCUMENTS 0010179 of 1980 European Pat. Off.
0077105 of 1983 European Pat. Off.

OTHER PUBLICATIONS

G. Vita, G. Bucher "Notiz Zur Darstellung aliphatischer Diamine" 1966.

Primary Examiner—Morton Foelak
Assistant Examiner—Richard Jones
Attorney, Agent, or Firm—John H. Shurtleff

[57] ABSTRACT

Process for preparing a pentane-1,5-diamine of the formula

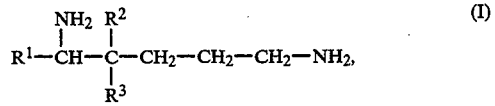

where
$R^1$ represents a variety of organic radicals including alkyl which can bear substituents such as hydroxyl, halogen, alkoxy, carbalkoxy, carboxyl, alkylamino, cycloalkyl or aryl, and
$R^2$ and $R^3$ independently of one another, represent hydrogen or have the same meanings as $R^1$ or together are a $C_4$-$C_7$-alkylene chain which is unsubstituted or substituted by one to five $C_1$-$C_4$-alkyl groups, which comprises:
(a) reacting a γ-cyanoketone of the formula

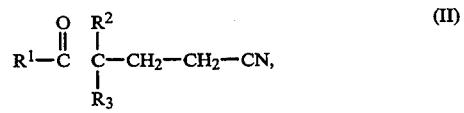

where $R^1$, $R^2$ and $R^3$ have the meanings given above, with excess ammonia in a first reaction space on an acidic heterogeneous catalyst at 20°-150° C. and 15-500 bar, and
(b) hydrogenating the resulting reaction product in a second separate reaction space in the presence of excess ammonia on a cobalt, nickel or noble metal catalyst at 50°-180° C. and 30-500 bar.

Novel pentane-1,5-diamines are obtained, in which $R^1$ must contain at least two carbon atoms if $R^2$ and $R^3$ are both hydrogen. These new compounds containing two primary amine groups possess advantageous properties of lower volatility and also greater asymmetry (with different reactivity of the two amine functions). They provide useful curing agents for epoxides and act as improved components of polyamides.

7 Claims, No Drawings

SELECTIVE PREPARATION OF LINEAR PENTANE-1,5-DIAMINES IN INCREASED YIELDS

The present invention relates to a novel process for the preparation of aliphatic pentane-1,5-diamines from gamma-cyanoketones, and to novel pentane-1,5-diamines.

Chem. Ber. 1966, 3387 to 3389 discloses the preparation of 1,5-diaminohexane from 5-oxocapronitrile. In this process, 1,5-diaminohexane is only obtained via the oxime intermediate by first reacting 5-oxocapronitrile with hydroxylamine hydrochloride in the presence of anhydrous sodium carbonate to give 5-oximinocapronitrile, which is subsequently reacted with lithium aluminum hydride to give the diamine; the overall yield is 42%. According to the authors, direct reductive amination of 5-oxocapronitrile gives the cyclization product, 2-methylpiperidine.

The fundamental problem of cyclization to give piperidines in the reductive amination of gamma-cyanoketones is described in Houben-Weyl, Volume 11/1, pages 357 to 359.

U.S. Pat. No. 4,429,157 describes a process for the preparation of primary monoamines and diamines for oxo compounds, which may also contain further reducible groups, using ammonia and hydrogen in the presence of known hydrogenation catalysts, in which the reaction with ammonia and hydrogen in the presence of hydrogenation catalysts is preceded by prereaction of the oxo compounds with ammonia at from 10° to 200° C. and from 1 to 300 bar in the presence of inorganic and organic ion exchangers in the ammonium form as imine-formation catalysts. In the examples, the process is restricted to the reductive amination of 3-cyano-3,5,5-trimethylcyclohexanone (isophorone nitrile) and 2,2,6,6-tetramethyl-4-piperidone (triacetonamine). Slight improvements in yield compared with the uncatalyzed procedure are achieved in the reductive amination of isophorone nitrile due to the use of the organic ion exchanger Lewatit SPR 120 in the imination (cf. comparative example 3 in U.S. Pat. No. 4,429,157: 90.3% yield with Lewatit SPR 120:93.9 to 94.7%).

Thus, there was hitherto no available process by which open-chain γ-cyanoketones can be converted into the corresponding open-chain pentane-1,5-diamines under industrially practicable conditions and in economically satisfactory yields.

It is an object of the present invention to provide a process for the preparation of pentane-1,5-diamines which overcomes the abovementioned disadvantages, to prepare pentane-1,5-diamines, in particular from γ-cyanoketones, under industrially practicable conditions in industrially satisfactory yields or space-time yields, and to prepare novel pentane-1,5-diamines with a higher degree of substitution than known 1,5-hexane diamine.

We have found that this object is achieved by a novel and improved process for the preparation of pentane-1,5-diamines of the formula I

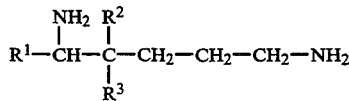
(I)

where $R^1$ is $C_1$- to $C_{20}$-alkyl, which is unsubstituted or substituted by one to four heterocyclic radicals or by $C_2$- to $C_8$-carbaloxy, carboxyl, $C_1$- to $C_8$-alkylamino and/or hydroxyl, or is $C_2$- to $C_{20}$-alkenyl, $C_3$- to $C_{20}$-cycloalkyl, $C_4$- to $C_{20}$-cycloalkylalkyl, $C_4$- to $C_{20}$-alkylcycloalkyl, $C_2$- to $C_{20}$-alkoxyalkyl, $C_2$- to $C_8$-alkoxycarbonyl, $C_1$- to $C_{20}$-haloalkyl, aryl, $C_7$- to $C_{20}$-aralkyl or $C_7$- to $C_{20}$-alkylaryl, and $R^2$ and $R^3$ independently of one another, are hydrogen, $C_1$- to $C_{20}$-alkyl, which is unsubstituted or substituted by one to four heterocyclic radicals or by $C_2$- to $C_8$-carbalkoxy, carboxyl, $C_1$- to $C_8$-alkylamino and/or hydroxyl, or are $C_2$- to $C_{20}$-alkenyl, $C_3$- to $C_{20}$-cycloalkyl, $C_4$- to $C_{20}$-cycloalkylalkyl, $C_4$- to $C_{20}$-alkylcycloalkyl, $C_2$- to $C_{20}$-alkoxyalkyl, $C_2$- to $C_8$-alkoxycarbonyl, $C_1$- to $C_{20}$-haloalkyl, aryl, $C_7$- to $C_{20}$-aralkyl or $C_7$- to $C_{20}$-alkylaryl, or together are a $C_4$- to $C_7$-alkylene chain which is unsubstituted or substituted by one to five $C_1$- to $C_4$-alkyl groups, from γ-cyanoketones of the formula II

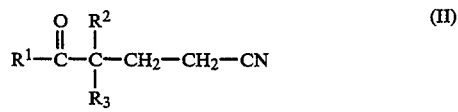
(II)

where $R^1$, $R^2$ and $R^3$ are as defined above, which comprises a) reacting the cyanoketones of the formula II with excess ammonia in a first reaction space on acidic heterogeneous catalysts at from 20° to 150° C. and at from 15 to 500 bar, and b) hydrogenating the resultant reaction products using hydrogen in a second reaction space in the presence of excess ammonia on cobalt-, nickel-, ruthenium-, palladium- and/or other noble metal-containing catalysts, with or without basic components, unsupported or on basic or neutral supports, at from 50° to 180° C. and at from 30 to 500 bar, in two spatially separate reaction spaces.

We have furthermore found pentane-1,5-diamines of the formula I'

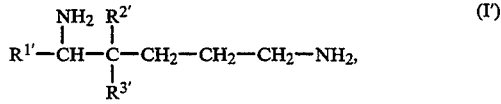
(I')

where $R^{1'}$ is $C_1$- to $C_{20}$-alkyl, which is unsubstituted or substituted by one to four heterocyclic radicals or by $C_2$- to $C_8$-carbalkoxy, carboxyl, $C_1$- to $C_8$-alkylamino and/or hydroxyl, or is $C_2$- to $C_{20}$-alkenyl, $C_2$- to $C_{20}$-alkynyl, $C_3$- to $C_{20}$-cycloalkyl, $C_4$- to $C_{20}$-cycloalkylalkyl, $C_4$- to $C_{20}$-alkylcycloalkyl, $C_2$- to $C_{20}$-alkoxyalkyl, $C_2$- to $C_8$-alkoxycarbonyl, $C_1$- to $C_{20}$-haloalkyl, aryl, $C_7$- to $C_{20}$-aralkyl or $C_7$- to $C_{20}$-alkylaryl, and $R^{2'}$ and $R^{3'}$ independently of one another, are hydrogen, $C_1$- to $C_{20}$-alkyl, which is unsubstituted or substituted by one to four heterocyclic radicals or by $C_2$- to $C_8$-carbalkoxy, carboxyl, $C_1$- to $C_8$-alkylamino and/or hydroxyl, or are $C_2$- to $C_{20}$-alkenyl, $C_2$- to $C_{20}$-alkynyl, $C_3$- to $C_{20}$-cycloalkyl, $C_4$- to $C_{20}$-cycloalkylalkyl, $C_4$- to $C_{20}$-alkylcycloalkyl, $C_2$- to $C_{20}$-alkoxyalkyl, $C_2$- to $C_8$-alkoxycarbonyl, $C_1$- to $C_{20}$-haloalkyl, aryl, $C_7$- to $C_{20}$-aralkyl or $C_7$- to $C_{20}$-alkylaryl, or together are a $C_4$- to $C_7$-alkylene chain which is unsubstituted or substituted by one to five $C_1$- to $C_4$-alkyl groups, with the proviso that $R^{1'}$ is not methyl if $R^{2'}$ and $R^{3'}$ are simultaneously hydrogen.

The process according to the invention can be carried out as follows in two spatially separate reaction spaces:

a) In a first step, the gamma-cyanoketones are reacted with excess ammonia at from 15 to 500 bar, preferably at from 30 to 350 bar, and at from 20° to 150° C., preferably at from 30° to 100° C. The condensation is carried out in the presence of acidic heterogeneous catalysts.

Suitable acidic heterogeneous catalysts are metal compounds having a Lewis acid or Brönstedt acid character, e.g. aluminum oxide, silicon dioxide, titanium dioxide or zirconium dioxide, furthermore phosphates, e.g. aluminum phosphates, or silicates, e.g. amorphous or crystalline aluminosilicates. Preference is given to aluminum oxide, titanium dioxide, zirconium dioxide and silicon dioxide, in particular aluminum oxide and titanium dioxide. The acidity of the catalysts may, if desired, be increased by doping with halides. Thus, for example, halogen-doped catalysts, such as chloride on aluminum oxide or chloride on titanium dioxide, are also used.

During the reaction of the $\gamma$-cyanoketones on the acidic heterogenous catalysts, a weight hourly space velocity of from 0.01 to 10, preferably from 0.05 to 7, particularly preferably from 0.1 to 5, kg of cyanoketone per kg of catalyst and per hour is maintained. It is expedient, but not absolutely essential, to employ from 5 to 500 mol, preferably from 10 to 400 mol, particularly preferably from 20 to 300 mol, of $NH_3$ per mol of cyanoketone. The reaction of the gamma-cyanoketones with ammonia can also be carried out in the presence of inert solvents, such as alkanols or tetrahydrofuran.

The reaction of the $\gamma$-cyanoketones can be carried out batchwise, but preferably continuously, e.g. in pressurized reactors or pressurized reactor cascades. In a particularly preferred embodiment, the $\gamma$-cyanoketones and $NH_3$ are passed through a tubular reactor in which the catalyst is arranged in the form of a fixed bed.

b) In a second process step, the resultant product is fed to a catalytic hydrogenation with from 3 to 10,000, preferably from 4 to 500, particularly preferably from 4.5 to 200, mol equivalents of hydrogen, if desired after introduction of further ammonia.

The hydrogenation is preferably carried out in liquid ammonia. From 5 to 500 mol, preferably from 10 to 400 mol, particularly preferably from 20 to 300 mol, of $NH_3$ are used per mol of gamma-cyanoketone employed in step 1. If necessary, the proportion of $NH_3$ can be increased to the desired value by introduction of $NH_3$.

The hydrogenation is generally carried out at 50° to 180° C., preferably at from 60° to 160° C., particularly preferably 70° to 140° C., and at from 30 to 500 bar, preferably from 50 to 350 bar, particularly preferably from 70 to 300 bar.

The weight hourly space velocity is expediently from 0.01 to 5 kg/(kg×h), preferably from 0.02 to 2.5 kg/(kg×h), particularly preferably from 0.05 to 2 kg/(kg×h).

In principle, any customary hydrogenation catalyst containing nickel, cobalt, iron, copper, ruthenium, palladium or another noble metal from sub-group VIII of the Periodic Table can be employed in the hydrogenation. Preference is given to ruthenium, cobalt or nickel catalysts. Particular preference is given to ruthenium and cobalt catalysts. The catalytically active metals can be employed as unsupported or supported catalysts. Examples of suitable supports are aluminum oxide, titanium dioxide, zirconium dioxide, zinc oxide and magnesium oxide and/or aluminum oxide. Preferred hydrogenation catalysts are those containing basic components, such as oxides and hydroxides of alkali metals and alkaline earth metals. The basic component is particularly preferably an oxide or hydroxide of an alkali metal, for example of sodium. If desired, the basic component may also be fed in during the hydrogenation process, for example as a solution of an alkali metal hydroxide or alkaline earth metal hydroxide in water.

The hydrogenation is particularly preferably carried out using cobalt, nickel or ruthenium with a basic component.

The reaction is preferably carried out continuously, for example in a pressure-tight stirred reactor or in a stirred-reactor cascade.

A particularly preferred embodiment employs tubular reactors, in which the material to be hydrogenated is passed upward or downward through a fixed catalyst bed.

Process steps a and b may likewise be carried out in a reactor containing imination catalysts and hydrogenation catalysts in two separate layers. In this case, the imination is expediently carried out in the presence of hydrogen.

After the hydrogenation, excess ammonia is removed, if necessary under pressure. The pentane-1,5-diamines obtained in this way can be isolated by fractional distillation. Substituted piperidines are only formed as by-products to a minor extent.

The starting materials for the process, the $\gamma$-cyanoketones, can be obtained, for example, from ketones and acrylonitrile.

The process according to the invention thus enables the conversion of $\gamma$-cyanoketones into pentane-1,5-diamines in high yield and space-time yield.

The substituents $R^1$, $R^2$ and $R^3$ in the compounds I and II have the following meanings:

$R^1$, $R^2$ and $R^3$ unbranched or branched $C_1$- to $C_{20}$-alkyl, preferably $C_1$- to $C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl and isooctyl, particularly preferably $C_1$- to $C_4$-alkyl, such as methyl, ethyl, n-propyl, isopropyl, n-butyl, isobutyl, sec-butyl and tert-butyl, unbranched or branched $C_1$- to $C_{20}$-alkyl which is substituted by one to four, preferably one to three, particularly preferably one or two, heterocyclic radicals, such as pyridyl, and/or by $C_2$- to $C_8$-carbalkoxy, carboxyl, $C_1$- to $C_8$-alkylamino and/or hydroxyl, preferably heteroaryl, particularly preferably pyridyl, $C_2$- to $C_{20}$-alkenyl, preferably $C_2$- to $C_8$-alkenyl, particularly preferably $C_2$- to $C_4$-alkenyl, such as vinyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl, $C_3$- to $C_{20}$-cycloalkyl, preferably $C_3$- to $C_8$-cycloalkyl, such as cyclopropyl, cyclobutyl, cyclopentyl, cyclohexyl, cycloheptyl and cyclooctyl, particularly preferably cyclopropyl, cyclopentyl, cyclohexyl and cyclooctyl,

- C₄- to C₂₀-cycloalkyl, preferably C₄- to C₁₂-cycloalkylalkyl, particularly preferably C₄- to C₈-cycloalkylalkyl, such as cyclopentylmethyl and cyclohexylmethyl,
- C₄- to C₂₀-alkylcycloalkyl, preferably C₄- to C₁₂-alkylcycloalkyl, particularly preferably C₄- to C₈-alkylcycloalkyl, such as methylcyclopentyl and methylcyclohexyl,
- C₁- to C₂₀-alkoxyalkyl, preferably C₁- to C₈-alkoxyalkyl, particularly preferably C₁- to C₅-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl and 1-methoxyethyl,
- C₁- to C₂₀-haloalkyl, preferably C₁- to C₈-haloalkyl, particularly preferably C₁- to C₄-fluoro- and/or chloroalkyl, such as fluoromethyl, difluoromethyl, trifluoromethyl, chloromethyl, dichloromethyl and trichloromethyl,
- aryl, such as phenyl, 1-naphthyl, 2-naphthyl, 1-anthryl, 2-anthryl and 9-anthryl, preferably phenyl, 1-naphthyl and 2-naphthyl, particularly preferably phenyl,
- C₇- to C₂₀- aralkyl, preferably C₇- to C₁₂-phenylalkyl, such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl,
- C₇- to C₂₀-alkylaryl, preferably C₇- to C₁₂-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl,
- C₂- to C₈-alkoxycarbonyl, preferably C₁- to C₄-alkoxycarbonyl, particularly preferably methoxycarbonyl and ethoxycarbonyl;

R² and R³ additionally, independently of one another, hydrogen, together, a cyclic or acyclic C₁- to C₇-alkylene chain which is unsubstituted or substituted by up to five C₁- to C₄-alkyl groups, e.g. =CH₂, =CH—CH₃, =C(CH₃)₂, —CH₂—CH₂—CH₂—, —(CH₂)₄—, —(CH₂)₅— and —(CH₂)₆—.

The substituents R¹', to R³' in the compounds I' are as defined for the substituents of R¹ to R³ in the compounds I, with the proviso that R¹' is not methyl if R²' and R³' are hydrogen.

Examples of preferred γ-cyanoketones of the formula II are: 5-oxohexanenitrile (from acetone), 4-methyl-5-oxohexanenitrile (from methyl ethyl ketone), 4-methyl-5-oxoheptanenitrile (from diethyl ketone), 4-ethyl-5-oxohexanenitrile (from methyl propyl ketone), 4,4,-dimethyl-5-oxohexanenitrile (from methyl isopropyl ketone), 4,4-dimethyl-5-oxoheptanenitrile (from ethylisopropyl ketone), 4,4,5-trimethyl-5-oxoheptanenitrile (from diisopropyl ketone), 4-isopropyl-5-oxohexanenitrile (from methyl isobutyl ketone), 4-isopropenyl-5-oxohexanenitrile, 4-isopropylidene-5-oxohexanenitrile (from methyl isobutenyl ketone), 6,6-dimethyl-5-oxoheptanenitrile (from pinacolone), 4-decyl-5-oxohexanenitrile (from methyl undecyl ketone), 4-(3-methylbutyl)-5-oxohexanenitrile (from 6-methyl-2-heptanone), 4-isobutyl-5-oxohexanenitrile (from 5-methyl-2-hexanone), 4-butyl-5-oxohexanenitrile (from 2-heptanone), 4-(2-methylbutyl)-5-oxohexanenitrile (from 5-methyl-2-heptanone), 5-phenyl-5-oxopentanenitril (from acetophenone), 4-benzyl-5-oxohexanenitrile (from 4-phenyl-2-butanone), 4,6-diphenyl-5-oxohexanenitrile (from dibenzyl ketone), 1-acetyl-1-cyanoethylcyclohexane (from cyclohexyl methyl ketone), 1-acetyl-1-cyanoethylcyclopropane (from cyclopropyl methyl ketone), 4,4-dimethyoxy-5-oxohexanenitrile (from methyl glyoxal dimethyl acetal), 4-methoxy-5-oxohexanenitrile (from methoxyacetone), 5-pyridyl-5-oxopentanenitrile (from acetylpyridine), 5-methoxycarbonyl-5-oxopentanenitrile (from methyl pyruvate) and 4-methoxycarbonyl-5-oxohexanenitrile (from ethyl acetoacetate).

Preferred pentane-1,5-diamines of the formulae I and I' are: hexane-1,5-diamine, 4-methylhexane-1,5-diamine, 4-methylheptane-1,5-diamine, 4-ethylhexane-1,5-diamine, 4,4-dimethylhexane-1,5-diamine, 4,4-dimethylheptane-1,5-diamine, 4,4,6-trimethylheptane-1,5-diamine, 4-isopropylhexane-1,5-diamine, 6,6-dimethylheptane-1,5-diamine 4-decylhexane-1,5-diamine, 4-(3-methylbutyl)hexane-1,5-diamine, 4-isobutylhexane-1,5-diamine, 4-butylhexane-1,5-diamine, 4-(2-methylbutyl)-hexane-1,5-diamine, 1-phenylpentane-1,5-diamine, 4-benzylhexane-1,5 -diamine, 4,6-diphenylhexane-1,5-diamine, 1-(1-aminoethyl)-1-(3-aminopropyl)cyclohexane, 1-(1-aminoethyl)-1-(3-aminopropyl)cyclopropane, 4,4-dimethoxyhexane-1,5-diamine, 4-methoxyhexane-1,5-diamine, 5-pyridylpentane-1,5-diamine, 5-methoxycarbonylpentane-1,5-diamine and 4-methoxycarbonylhexane-1,5-diamine.

Due to the higher degree of substitution, the diamines claimed have lower volatility and greater asymmetry (different reactivity of the amine functions) than known 1,5-hexanediamine. This results in, inter alia, better processing properties of the diamines, for example as components (curing agents) for epoxides and components for polyamides, and lower odor nuisance caused by unreacted diamines and the diisocyanates which can be prepared therefrom.

EXAMPLES

Example 1

A vertical tubular reactor (diameter 16 mm, fill level 50 cm, oil-heated twin jacket) was filled with 90.1 g (87 ml) of a catalyst containing 3% of ruthenium on β-aluminum oxide in the form of 1.2 mm pellets (catalyst preparation by impregnating the pores of β-aluminum oxide with aqueous ruthenium nitrate solution, and drying the catalyst at 120° C.). In order to reduce the catalyst, the temperature was, at 100 bar while simultaneously passing 150 l (s.t.p.)/h of hydrogen through the reactor, increased stepwise from 100° to 220° C. over the course of 7 hours and then kept at 220° C. for 9 hours.

20.5 g of 5-oxohexanenitrile (purity 97.7%) and 240 g of liquid ammonia were pumped hourly at 250 bar at 80° C. through a tubular reactor (diameter 16 mm, fill level 50 cm, oil-heated twin jacket) arranged before the hydrogenation reactor and filled with 65.3 g (100 ml) of titanium dioxide (anatase) in the form of 1.5 mm pellets, at 250 bar at 80° C. The discharged product was subsequently passed from bottom to top through a hydrogenation reactor at 250 bar and 110° C. while simultaneously passing 100 l (s.t.p)/h of hydrogen through the reactor. The mixture was decompressed to atmospheric pressure, NH₃ was removed by distillation, and the hydrogenation product was analyzed by means of quantitative gas chromatography, giving a 1,5-hexanediamine yield of 87% and a 2-methylpiperidine yield of 8%.

Example 2

A vertical tubular reactor (diameter 16 mm, fill level 50 cm, oil-heated twin jacket) was filled with 177 g (100 ml) of a basic unsupported cobalt catalyst (CoO containing 5% of $Mn_2O_3$ and 1.4% of $Na_2O$) in the form of 1 to 1.5 mm grit. In order to reduce the catalyst, the temperature was, at 100 bar while simultaneously passing 150 l (s.t.p.)/h hydrogen through the reactor, increased stepwise from 100° to 330° C. over the course of 23 hours and then kept at 330° C. for 30 hours.

20.5 g of 5-oxohexanenitrile (purity 97.7%) and 100 g of liquid ammonia were pumped hourly from bottom to top at 250 bar and 80° C. through a tubular reactor (diameter 16 mm, fill level 50 cm, oil-heated twin jacket) arranged before the hydrogenation reactor and filled with 70.0 g (100 ml) of γ-aluminum oxide in the form of 1.5 mm pellets. 100 l (s.t.p.)/h of hydrogen were subsequently passed in, and the product discharged from the upstream imination reactor was passed through the hydrogenation reactor from bottom to top at 250 bar and 110° C. The mixture was decompressed to atmospheric pressure, and the ammonia was removed by distillation. According to analysis of the hydrogenation product by gas chromatography, the yield of 1,5-hexanediamine was 96% and 2-methylpiperidine was formed in a yield of 2%.

Example 3

A vertical tubular reactor (diameter 16 mm, fill level 50 cm, oil-heated twin jacket) was filled with 176.7 g (100 ml) of a basic unsupported cobalt catalyst (CoO containing 5% of $Mn_2O_3$ and 1.4% of $Na_2O$) in the form of 1 to 1.5 mm grit, and the catalyst was reduced as in Example 2.

20.5 g of 5-oxohexanenitrile (purity 97.7%) and 340 g of liquid ammonia were pumped hourly from bottom to top at 250 bar and 80° C. through a tubular reactor (diameter 16 mm, fill level 20 cm, oil-heated twin jacket) arranged before the hydrogenation reactor and filled with 25.4 g (40 ml) of titanium dioxide (anatase) in the form of 1.5 mm pellets. 100 l (s.t.p.)/h of hydrogen were subsequently passed in, and the product discharged from the upstream imination reactor was passed through the hydrogenation reactor from bottom to top at 250 bar and 110° C. The mixture was decompressed to atmospheric pressure, the ammonia was removed by distillation, and the hydrogenation product from 75 hours was separated by fractional distillation on a 30 cm packed column (3-mm glass rings). 1400 g of 1,5-hexanediamine, corresponding to a yield of 89%, were obtained.

Example 4

A vertical tubular reactor (diameter 16 mm, fill level 50 cm, oil-heated twin jacket) was filled with 177 g (100 ml) of a basic unsupported cobalt catalyst (CoO containing 5% of $Mn_2O_3$ and 1.4% of $Na_2O$) in the form of 1 to 1.5 mm grit, and the catalyst was reduced as in Example 2.

21 g of 4,4-dimethyl-5-oxohexanenitrile (purity 97.2%) and 180 g of liquid ammonia were pumped hourly from bottom to top at 250 bar and 80° C. through a tubular reactor (diameter 0.16 mm, fill level 50 cm, oil-heated twin jacket) arranged before the hydrogenation reactor and filled with 63.5 g (100 ml) of titanium dioxide (anatase). in the form of 1.5 mm pellets. 100 l (s.t.p.)/h of hydrogen were subsequently passed in, and the product discharged from the upstream imination reactor was passed through the hydrogenation reactor from bottom to top at 250 bar and 110° C. The mixture was decompressed at atmospheric pressure, and the ammonia was removed by distillation. The discharge from 24 hours was separated by fractional distillation on a 30 cm packed column (3-mm glass rings). 445 g of 4,4-dimethyl-1,5-hexanediamine were obtained as a colorless liquid (b.p. 90° C./3 mbar), corresponding to a yield of 88%.

Example 5

A vertical tubular reactor (diameter 16 mm, fill level 50 cm, oil-heated twin jacket) was filled with 177 g (100 ml) of a basic unsupported cobalt catalyst (CoO containing 5% of $Mn_2O_3$ and 1.4% of $Na_2O$) in the form of 1 to 1.5 mm grit, and the catalyst was reduced as in Example 2.

10 g of 4,4,-dimethyl-5-oxohexanenitrile (purity 97.2%) and 195 g of liquid ammonia were pumped hourly from bottom to top at 250 bar and 80° C. through a tubular reactor (diameter 16 mm, fill level 50 cm, oil-heated twin jacket) arranged before the hydrogenation reactor and filled with 63.5 g (100 ml) of titanium dioxide (anatase) in the form of 1.5 mm pellets. 100 l (s.t.p.)/h of hydrogen were subsequently passed in, and the product discharged from the upstream imination reactor was passed through the hydrogenation reactor from bottom to top at 250 bar and 110° C. The mixture was decompressed to atmospheric pressure, the ammonia was removed by distillation, and the hydrogenation product was analyzed quantitatively by means of gas chromatography, giving a yield of 93.0% of 4,4-dimethyl-1,5-hexanediamine and 4.5% of 2,3,3-trimethylpiperidine.

Example 6

A vertical tubular reactor (diameter 16 mm, fill level 50 cm, oil-heated twin jacket) was filled with 177 g (100 ml) of a basic unsupported cobalt catalyst (CoO containing 5% of $Mn_2O_3$ and 1.4% of $Na_2O$) in the form of 1 to 1.5 mm grit, and the catalyst was reduced as in Example 2.

10 g of 4-isopropyl-5-oxohexanenitrile (purity 95.7%) and 115 g of liquid ammonia were pumped hourly from bottom to top at 250 bar and 80° C. through a tubular reactor (diameter 16 mm, fill level 50 cm, oil-heated twin jacket) arranged before the hydrogenation reactor and filled with 63.5 g (100 ml) of titanium dioxide (anatase) in the form of 1.5 mm pellets. 100 l (s.t.p.)/h of hydrogen were subsequently passed in, and the product discharged from the upstream imination reactor was passed through the hydrogenation reactor from bottom to top at 250 bar and 110° C. The mixture was decompressed at atmospheric pressure, the ammonia was removed by distillation, and the discharge from 72 hours was separated by fractional distillation on a 30 cm packed column (3-mm glass rings). 640 g of 4-isopropyl-1,5-hexanediamine were obtained as a colorless liquid (b.p. 80° C./1 mbar), corresponding to a yield of 90%.

We claim:

1. A process for the selective preparation in increased yields of open-chain pentane-1,5-diamines of the formula I

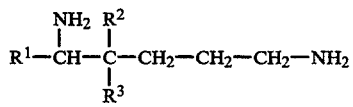

where
R$^1$ is C$_1$- to C$_{20}$-alkyl, which is unsubstituted or substituted by one to four heterocyclic radicals or by C$_2$- to C$_8$-carbalkoxy, carboxyl, C$_1$- to C$_8$-alkylamino or hydroxyl, or is C$_2$- to C$_{20}$-alkenyl, C$_3$- to C$_{20}$-cycloalkyl, C$_4$- to C$_{20}$-cycloalkylalkyl, C$_4$- to C$_{20}$-alkylcycloalkyl, C$_2$- to C$_{20}$-alkoxyalkyl, C$_2$- to C$_8$-alkoxycarbonyl, C$_1$- to C$_{20}$-haloalkyl, aryl, C$_7$- to C$_{20}$-aralkyl or C$_7$- to C$_{20}$-alkylaryl, and R$^2$ and R$^3$, independently of one another, are hydrogen, C$_1$- to C$_{20}$-alkyl, which is unsubstituted or substituted by one to four heterocyclic radicals or by C$_2$- to C$_8$-carbalkoxy, carboxyl, C$_1$- to C$_8$- alkylamino or hydroxyl, or are C$_4$- to C$_{20}$-alkenyl, C$_3$- to C$_{20}$-cycloalkylalkyl, C$_2$- to C$_{20}$-alkoxyalkyl, C$_2$- to C$_8$-alkoxycarbonyl, C$_1$- to C$_{20}$-haloalkyl, aryl, C$_7$- to C$_{20}$-aralkyl or C$_7$- to C$_{20}$-alkylaryl, or together are a C$_4$- to C$_7$-alkylene chain which is unsubstituted or substituted by one to five C$_1$- to C$_4$-alkyl groups, from γ-cyanoketones of the formula II

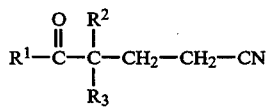

where R$^1$, R$^2$ and R$^3$ are as defined above, which comprises the steps of:

a) reacting the cyanoketones of the formula II with excess ammonia in a first reaction space on an acidic heterogeneous catalyst selected from the group consisting of the oxides of aluminum, silicon, titanium and zirconium or their corresponding halogen-doped oxides, aluminum phosphates and aluminum silicates at from 20° to 150° C. and at from 15 to 500 bar; and b) hydrogenating the resultant reaction products using hydrogen in a second reaction space in the presence of excess ammonia on cobalt-, nickel-, ruthenium-, palladium- or other noble metal-containing catalysts, with or without basic components, unsupported or on basic or neutral supports, at from 50° to 180° C. and at from 30 to 500 bar, the two steps being carried out in two spatially separate reaction spaces.

2. A process as claimed in claim 1, wherein the acidic heterogeneous catalyst is selected from the group consisting of aluminum oxide, titanium dioxide, zirconium dioxide and silicon dioxide.

3. A process as claimed in claim 1, wherein the acidic heterogeneous catalyst is titanium dioxide.

4. A process as claimed in claim 1, wherein the acidic heterogeneous catalyst is γ-aluminum oxide.

5. A process at claimed in claim 1, wherein the excess of ammonia in reaction a) is 10 to 400 mols per mol of cyanoketone.

6. A process as claimed in claim 1, wherein the excess of ammonia in reaction a) is 20 to 300 mols per mol of cyanoketone.

7. A process as claimed in claim 1, wherein the hydrogenation in reaction b) is carried out in liquid ammonia in an amount of from 5 to 500 mols per mol of γ-cyanoketone used in reaction a).

* * * * *